(12) United States Patent
Frigg et al.

(10) Patent No.: US 6,893,443 B2
(45) Date of Patent: May 17, 2005

(54) ANGLE-ADJUSTABLE BONE SCREW AND FIXATION DEVICE

(75) Inventors: Robert Frigg, Bettlach (CH); Robert Ferus, Bettlach (CH)

(73) Assignee: Synthes (U.S.A)

( * ) Notice: Subject to any disclaimer, the term of this patent is extended or adjusted under 35 U.S.C. 154(b) by 145 days.

(21) Appl. No.: 10/036,531

(22) Filed: Jan. 7, 2002

(65) Prior Publication Data

US 2003/0036758 A1 Feb. 20, 2003

Related U.S. Application Data

(63) Continuation of application No. PCT/CH99/00302, filed on Jul. 7, 1999.

(51) Int. Cl.[7] .............................................. A61B 17/70
(52) U.S. Cl. .......................................... 606/61; 606/73
(58) Field of Search ........................ 606/61, 59, 72, 606/73; 403/90, 274, 284; 623/17.14; 411/371.2, 533, 81

(56) References Cited

U.S. PATENT DOCUMENTS

| | | | |
|---|---|---|---|
| 4,299,212 A | 11/1981 | Goudfrooy ................ 128/92 A |
| 4,653,481 A | 3/1987 | Howland et al. ............. 128/69 |
| 4,763,644 A | 8/1988 | Webb ......................... 128/69 |
| 4,790,297 A | 12/1988 | Luque ........................ 128/69 |
| 4,887,596 A | 12/1989 | Sherman ..................... 606/61 |
| 5,042,982 A | 8/1991 | Harms et al. ................ 606/61 |
| 5,084,048 A | 1/1992 | Jacob et al. ................. 606/61 |
| 5,092,867 A | 3/1992 | Harms et al. ................ 606/61 |
| 5,129,388 A | 7/1992 | Vignaud et al. ............. 606/61 |
| 5,129,900 A | 7/1992 | Asher et al. ................. 606/61 |
| 5,147,360 A | 9/1992 | Dubousset ................... 606/61 |
| 5,154,719 A | 10/1992 | Cotrel ........................ 606/73 |
| 5,176,678 A | 1/1993 | Tsou .......................... 606/61 |
| 5,176,680 A | 1/1993 | Vignaud et al. ............. 606/61 |
| 5,190,543 A | 3/1993 | Schläpfer .................... 606/61 |
| 5,196,013 A | 3/1993 | Harms et al. ................ 606/61 |
| 5,207,678 A | 5/1993 | Harms et al. ................ 606/61 |
| 5,217,497 A | 6/1993 | Mehdian ..................... 623/17 |
| 5,234,431 A | 8/1993 | Keller ........................ 606/70 |
| 5,257,993 A | 11/1993 | Asher et al. ................. 606/61 |
| 5,261,907 A | 11/1993 | Vignaud et al. ............. 606/60 |
| 5,261,912 A | 11/1993 | Frigg ......................... 606/61 |
| 5,306,275 A | 4/1994 | Bryan ........................ 606/61 |
| 5,312,404 A | 5/1994 | Asher et al. ................. 606/61 |
| 5,364,399 A | * 11/1994 | Lowery et al. .............. 606/69 |
| 5,385,583 A | 1/1995 | Cotrel ........................ 623/17 |
| 5,423,818 A | 6/1995 | Van Hoeck et al. ......... 606/61 |
| 5,429,639 A | 7/1995 | Judet ......................... 606/61 |
| 5,443,467 A | 8/1995 | Biedermann et al. ........ 606/65 |
| 5,466,237 A | 11/1995 | Byrd, III et al. ............. 606/61 |
| 5,474,555 A | 12/1995 | Puno et al. .................. 606/73 |
| 5,496,321 A | 3/1996 | Puno et al. .................. 600/61 |
| 5,549,608 A | 8/1996 | Errico et al. ................ 606/61 |

(Continued)

FOREIGN PATENT DOCUMENTS

| | | |
|---|---|---|
| EP | 0 507 162 A1 | 8/1993 |
| WO | 0 498 709 A1 | 8/1992 |
| WO | WO 98/34553 | 8/1998 |
| WO | WO 98/41160 | 9/1998 |
| WO | WO99/03415 | 1/1999 |

*Primary Examiner*—Todd E. Manahan
*Assistant Examiner*—David Comstock
(74) *Attorney, Agent, or Firm*—Jones Day

(57) ABSTRACT

The invention is related to a bone screw and a device for osteosynthetic fixation. The bone screw includes a head, a shank, and a collar disposed therebetween. A plate or bone fixation assembly may be provided with at least one bore configured and dimensioned to receive such a bone screw, the bore including a tapered wall portion. When the screw is received in the bore and the collar abuts the tapered wall portion, the screw may be disposed at a variety of angles with respect to the plate and fixed at a selected angle.

69 Claims, 5 Drawing Sheets

U.S. PATENT DOCUMENTS

| | | |
|---|---|---|
| 5,554,157 A | 9/1996 | Errico et al. .................. 606/61 |
| 5,562,663 A | 10/1996 | Wisnewski et al. ........... 606/61 |
| 5,575,792 A | 11/1996 | Errico et al. .................. 606/61 |
| 5,578,033 A | 11/1996 | Errico et al. .................. 606/61 |
| 5,584,834 A | 12/1996 | Errico et al. .................. 606/61 |
| 5,586,984 A | 12/1996 | Errico et al. .................. 606/61 |
| 5,609,593 A | 3/1997 | Errico et al. .................. 606/61 |
| 5,609,594 A | 3/1997 | Errico et al. .................. 606/61 |
| 5,733,285 A | 3/1998 | Errico et al. .................. 606/61 |
| 5,735,853 A * | 4/1998 | Olerud ........................ 606/71 |
| 5,743,669 A * | 4/1998 | Fujita et al. ................ 403/131 |
| 5,782,833 A * | 7/1998 | Haider ........................ 606/61 |
| 6,146,383 A * | 11/2000 | Studer et al. ................. 606/61 |
| 6,193,721 B1 * | 2/2001 | Michelson .................. 606/70 |

* cited by examiner

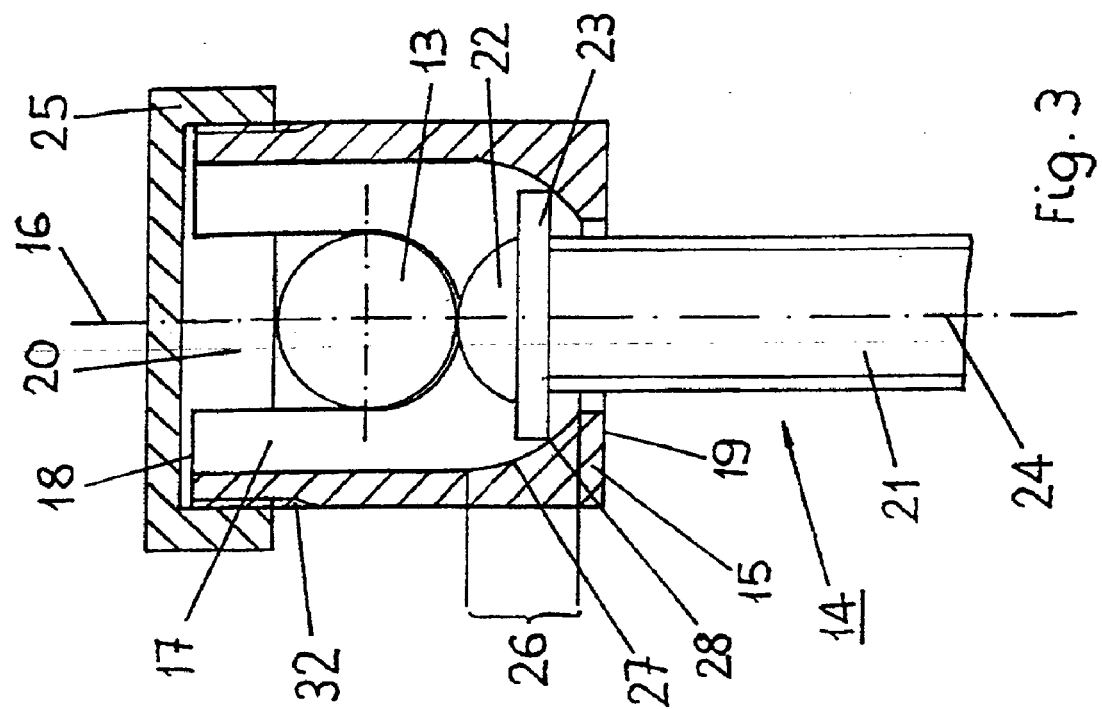
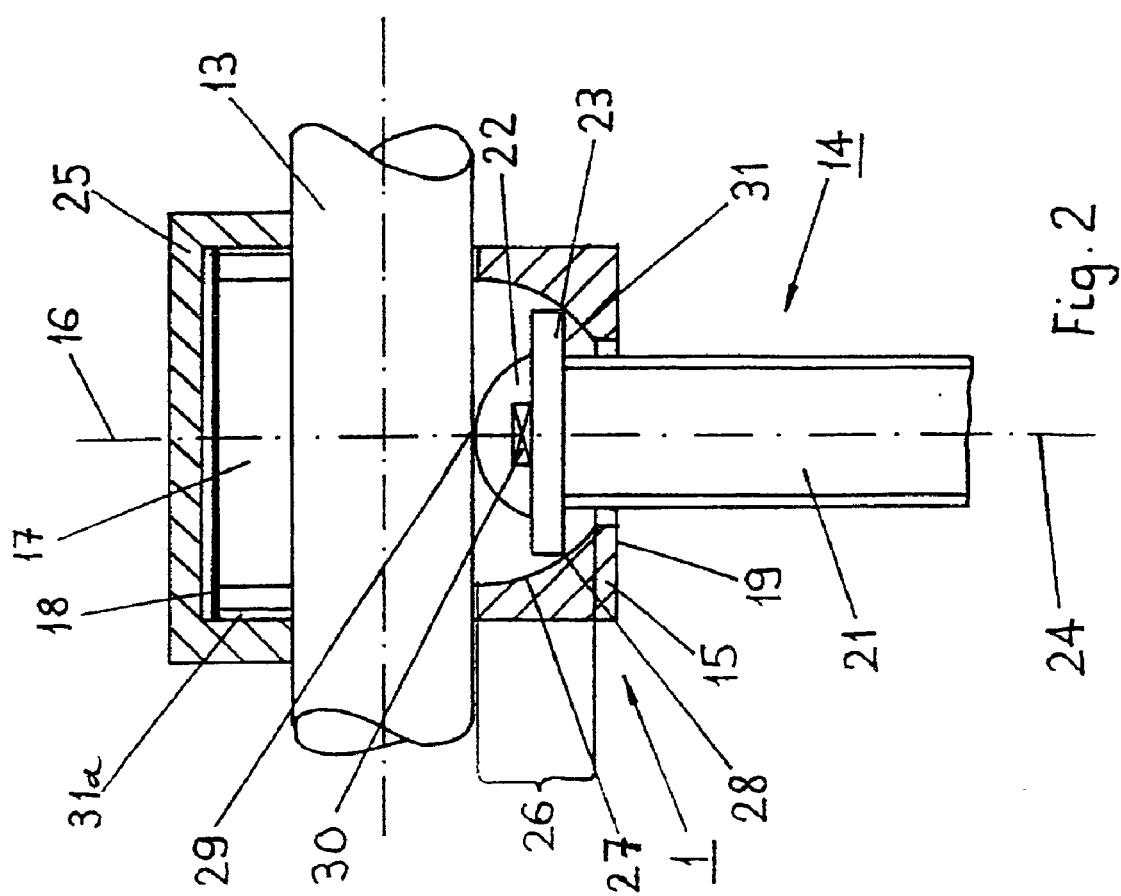

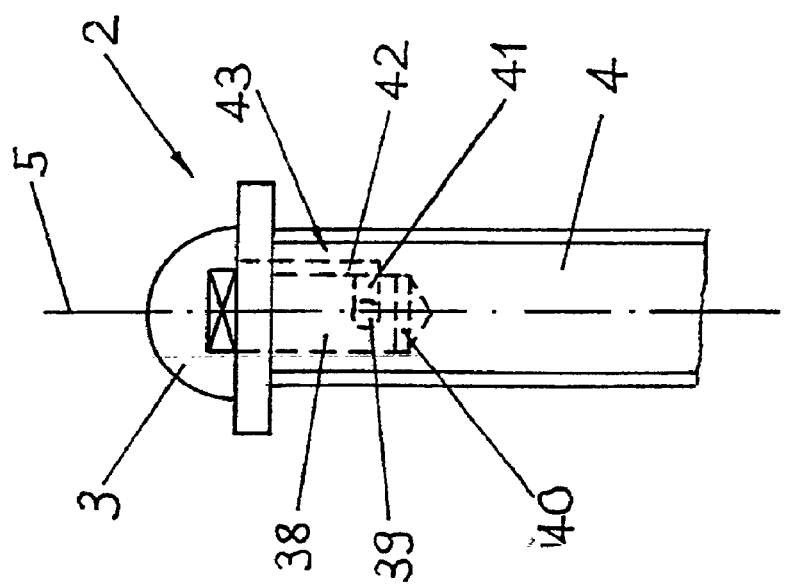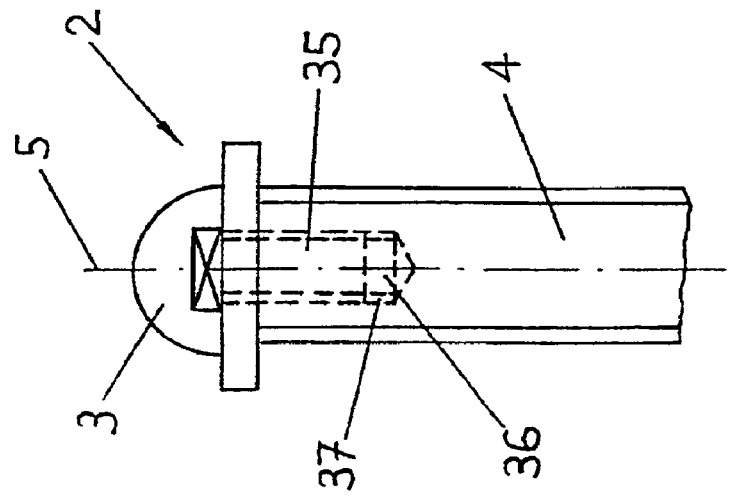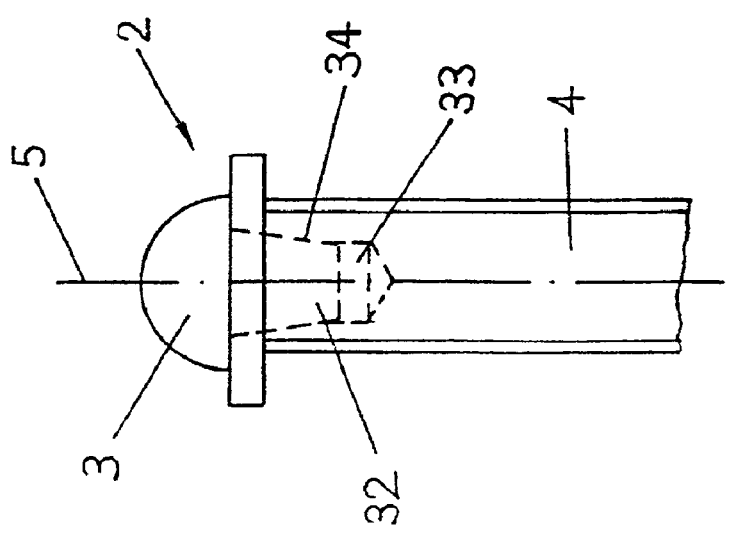

US 6,893,443 B2

ANGLE-ADJUSTABLE BONE SCREW AND FIXATION DEVICE

CROSS-REFERENCE TO RELATED APPLICATIONS

This application is a continuation of the U.S. national stage designation of copending International Patent Application PCT/CH99/00302, filed Jul. 7, 1999, the entire content of which is expressly incorporated herein by reference thereto.

FIELD OF THE INVENTION

The present invention relates generally to orthopaedic fixation devices, and in particular to a fixation system for vertebral bodies.

BACKGROUND OF THE INVENTION

Various devices for internal fixation of bone fragments in a human or animal body are known in the prior art. In the case of internal fixation of the spinal column or of parts of the spinal column, such devices often essentially comprise pedicle screws which are anchored by means of threads into the pedicles of the individual vertebrae to be joined, and one or more longitudinal supports which extend in the direction of the spinal column and have to be connected securely to the pedicle screws. To achieve stable anchoring of the whole implant, the pedicle screws must on the one hand be screwed securely into the pedicles and, on the other hand, be connected rigidly to the longitudinal supports.

The connection between the screw head of the pedicle screws and the longitudinal support is normally effected by means of clamp mechanisms which typically must permit a stable connection, even at different angles of the pedicle screw in relation to the longitudinal support. The clamp connection typically must be releasable so that the whole implant can be removed again without leaving large tissue openings in the area of the spinal column. Secure connections between bone screws and plates or supports are also common in other internal bone fixations. For such devices, different angles of the bone screws relative to the plate or the support are desired without adversely affecting the connections in terms of their stability.

For instance, one bone-anchoring screw and stabilizer rod connection for the internal fixation of vertebrae is known from U.S. Pat. No. 5,466,237 to Byrd. A bone-anchoring screw is provided with a screw head which is designed as a segment of a sphere on its side facing the screw shank and is convex at its end. The spherical segment part of the screw is mounted in a bore of the anchoring element, the bore comprising a concave portion which tapers toward the screw shank so that a ball-joint-type connection is obtained between the bone screw and the anchoring element. The ball-joint-type connection is blocked by tightening a nut on the anchoring element. The nut presses against the longitudinal support which has been placed in the anchoring element and which consequently presses against the terminal convex part of the screw head and thus blocks the screw head in the anchoring element. However, because of the often inexactly matching spherical surfaces on the bone screw and in the anchoring element, such a blockable ball-joint-type connection is unsuitable for taking up the forces which arise in bone fixation. In addition, such a ball-joint-type connection can only be blocked with frictional engagement.

Despite this development, a need exists for a stable connection between a bone fastener and an anchoring element which permits different angles between the screw axis and anchoring element and which may permit a form fit with suitable material pairing.

SUMMARY OF THE INVENTION

The invention in one embodiment is related to a bone fixation assembly having a bone fastener comprising a head, a shank, and a collar, and a receiving member comprising at least one bore that defines an inner surface. The collar may have a top portion and a plurality of lower portions, with at least two adjacent lower portions forming an edge. The collar and inner surface may contact one another along the edge. The at least one edge may generally define a ring. Alternatively, the at least one edge may comprise two edges which each generally define a ring. The rings may be concentric. Each edge of the collar generally defines a ring. For example, the at least one edge may define a plurality of concentric rings.

The bone fixation assembly may include a fastener which is disposed about a longitudinal axis. The at least one bore may also be disposed about a central axis. The fastener may be positionable so that the longitudinal axis is transverse to the central axis when the collar of the fastener abuts the inner surface of the bore. Also, the bone fixation assembly may have at least one bore with first and second portions. The first portion may have a substantially constant diameter and the second portion may have a plurality of different diameters. The second portion may be concave and have a radius of curvature. The ratio of half the diameter of the first portion to the radius of curvature may be between about 0.5 and about 1.0. For example, the ratio of half the diameter of the first portion to the radius of curvature might be between about 0.85 and about 0.95.

The fastener may have a longitudinal axis and the collar may have generally circular cross-section transverse to the longitudinal axis. For instance, the collar may have a substantially constant diameter. More particularly, the collar diameter may be between about 4 mm and about 10 mm. Also, the collar may have a thickness defined between the top portion and a lowest of the lower portions between about 0.5 mm and about 2 mm.

The fastener head may be convex with respect to the shank. For instance, the fastener head may be substantially semispherical. The fastener head may also be integrally formed with the shank, or removably attached to the shank.

The bone fixation assembly may further include a clamping member. The clamping member may be capable of locking the bone fastener with respect to the receiving member in a fixed configuration. For instance, the clamping member may be a grub screw, or other suitable locking mechanism. The clamping member may be releasably associated with the receiving member for releasably locking the assembly in a fixed configuration. The clamping member may be threadably associated with the receiving member.

The bone fixation assembly may also have an inner surface with a deformable material such that a form-fit connection is obtainable between the collar and receiving member.

Additionally, the bone fixation assembly may have a receiving member which further comprises a channel extending transverse to a central axis of the bore. The channel may be configured and dimensioned to receive a longitudinal support. The bone fixation assembly may further include a longitudinal support.

The invention in one embodiment is also related to a device for osteosynthetic bone fixation. The device may include a bone fastener comprising a collar and a shank, the collar having a top portion and a plurality of lower portions, at least two adjacent lower portions forming at least one edge. The device may further include a receiving member with at least one bore. The bore may define an inner surface with a first cylindrical portion and a second non-cylindrical portion. The at least one edge may abut the non-cylindrical portion at a selectable angle.

The bone fastener may have a longitudinal axis and the collar may be disposed generally concentric to the longitudinal axis. The at least one edge may be disposed generally concentric to the longitudinal axis. In addition, the at least one edge may be substantially circular with each of the at least one edge being disposed along an imaginary convex surface. For instance, the imaginary convex surface may be spherical.

The collar may also have a substantially constant diameter. For instance, the diameter may be between about 4 mm and about 10 mm. And, the collar may have a thickness defined between the top portion and a lowest of the lower portions, for example, between about 0.5 mm and about 2 mm.

The bone fastener may further comprise a head that is convex with respect to the shank, and at least a portion of the head may be substantially semispherical. The head may be integrally formed with the shank, or the fastener head may be removably attached to the shank.

The device may also have a clamping member, and the collar may be releasably lockable by the clamping member. For instance, the clamping member may be a grub screw. The clamping member may also be a nut. The receiving member may further include a channel extending transverse to a central axis of the bore, the channel configured and dimensioned to receive a longitudinal support. The device may also include a longitudinal support.

The invention in another embodiment is also related to a bone screw comprising a head, a shank, and a collar disposed between the head and shank and comprising a top portion and a plurality of lower portions. At least two adjacent lower portions of the collar form at least one edge generally concentric to a longitudinal axis of the bone screw. Each edge also may be disposed along an imaginary convex surface that is generally spherical. For instance, the collar may have two edges. In addition, each edge may have a diameter, and the diameters of the edges might decrease as a function of increasing distance from the head.

The bone screw may have a collar which is disk-shaped. The head may be convex with respect to the shank. At least a portion of the head may be substantially semispherical. The head may be integrally formed with the shank. Alternatively, the head and shank may be separately formed, and the head may be releasably associated with the shank. The head may be threadably associated with the shank. The head may be connected to the shank by a conical peg that is received in a conical bore, with the conical peg and conical bore being disposed along the longitudinal axis, or the head may be connected to the shank by a bayonet lock. The head may further comprise a zenith disposed on the longitudinal axis.

Each edge of the bone screw may form a generally circular shape having a diameter between, for example, about 4 mm and about 10 mm. More particularly, each edge may form a generally circular shape having a diameter between, for example, about 8 mm and about 10 mm. The collar may have a thickness defined between a top surface and a bottom surface between, for example, about 0.5 mm and about 2 mm. And, the shank may have an external diameter between, for example, about 3 mm and about 6 mm. Each edge may also form a substantially circular shape, and each edge of the bone screw may be substantially sharp.

The bone screw according to one embodiment of the invention comprises a screw shank to be anchored concentric to a longitudinal axis in a bone or bone part, and a concentric screw head, and also, between the screw head and screw shank, a disk-shaped collar which is concentric to the longitudinal axis. The diameter, circumference or outer periphery of the collar may be greater than the diameter of the screw shank. Depending on the embodiment of the bone screw, the diameter of the collar preferably may be between, for example, 8 mm and 10 mm or between 4 mm and 6 mm, while the diameter of the screw shank preferably may be between, for example, 5 mm and 6 mm or between 3 mm and 5 mm. The thickness of the collar, again depending on the embodiment of the bone screw, preferably may be between, for example, 1 mm and 2 mm or between 0.5 mm and 1 mm.

The rim of the collar preferably may be stepped and have a lower edge for bearing against the wall of a bore formed with a curved surface.

In another embodiment of the bone screw, the collar comprises, on the side toward the screw shank, a plurality of circular edges concentric to the longitudinal axis of the screw, with diameters $d > d_1 > d_2$ decreasing toward the screw shank. The diameters $d$, $d_1$, $d_2$ are preferably dimensioned such that the edges run on an imaginary convex surface on the screw shank side. In a further embodiment of the bone screw, this imaginary surface may be designed as a spherical zone concentric to the central axis and with a radius Y. The screw head may be of convex design, in particular spherical or semispherical.

Depending on the embodiment, the screw head and screw shank may be formed as one piece or in more than one piece. The screw head may be securable in a releasable manner on the screw shank by means of a cone connection, a screw connection or a bayonet lock connection, or by other suitable connections.

Depending on the embodiment, the bone screw may be used for fixation of bones or bone parts in an osteosynthesis fixation device and may serve, for example, for the fixation of bones or bone parts on a bone plate or for fixation of vertebrae in a spinal column fixation device.

The device according to one embodiment of the invention for osteosynthetic bone fixation comprises at least one bone screw with a screw shank to be anchored in the bone or bone part and with a screw head, and at least one fixation body which serves for stable fixation of the bones or bone parts. The fixation body has at least one bore for receiving the bone screw, this bore passing through the fixation body and comprising a concave portion tapering toward the end at the screw shank side. The bone screw may have a disk-shaped collar arranged between screw head and screw shank and concentric to the longitudinal axis of the bone screw. The diameter of the collar may be dimensioned such that the collar, in the concave portion of the bore, can be made to bear on the wall of the bore at different angles between the longitudinal axis of the bone screw and the central axis of the bore. This configuration of the disk-shaped collar with a plane surface on the screw shank side, which surface bears on the concave wall of the bore upon tightening of the screw, permits a linear contact between the bone screw and the fixation body.

In one embodiment of the device, a longitudinal support is connected to a bone screw, designed as a pedicle screw, within a spinal column fixation system. The fixation body may be designed as a receiving head which serves to connect the longitudinal support to the pedicle screw. In addition to the through-bore passing through the receiving head in order to receive the pedicle screw, there may be a channel extending transverse to the central axis of the receiving head and open toward the screw head end in order to receive the longitudinal support. The device additionally comprises clamping means which can be connected to the receiving head in a releasable manner at the screw head end and serve for fixing the longitudinal support and the pedicle screw within the receiving head. The through-bore may comprise a concave portion tapering toward its screw shank end, so that the collar on the pedicle screw can be made to bear on the wall of the through-bore, in the concave portion of the through-bore, at different angles between the screw axis and the central axis of the bore.

In a further embodiment of the device, the disk-shaped collar on the bone screw may have a diameter d, and the concave portion may be of spherical design and have a diameter D, where D=d. However, with this design, only small angles of the screw axis relative to the central axis of the bore in the fixation body are possible, since otherwise linear contact is obtained only on one part of the collar circumference. For greater angles, a design of the concave portion is suitable with a diameter D, where D>d. In this case, the ratio d:D can be chosen, for example, between 0.5 and 1.0, preferably between 0.85 and 0.95. In addition, the diameter of the screw head may be chosen such that, if the bone screw is in an inclined position, the screw head does not bear on the wall of the bore and thereby restrict an inclined position of the bone screw.

In yet another embodiment of the device, the concave portion may be designed in the manner of a spherical segment, where the spherical segment has a radius X while the diameter of the concave portion is D, so that $X \geq D/2$. The ratio of D/2 to X may be, for example, between 0.5 and 1.0, preferably between 0.85 and 0.95.

In a particular embodiment of the device, the convex screw head of the bone screw is of spherical or semispherical design. In the case of the connection device between the longitudinal support and pedicle screw, the advantage of this design lies in the fact that a longitudinal support clamped between screw head and clamping means presses on the screw head concentric to the central axis even if the pedicle screw is in an inclined position.

In one embodiment of a multiple-piece bone screw, the screw shank is fitted with a bore having a screw thread which allows a screw head having a mating external screw thread to be advanced into the bore and locked in place to form a complete bone screw. The screw head may be fitted with a means for advancing the screw head into the bone. Non limiting examples of such means include: a socket for receiving the tip of a screw driver, or a hexagon socket. In another embodiment, the screw head is configured and dimensioned to be received within a bore, which comprises a hexagon socket. In the case of a central arrangement of, for example, a hexagon socket in the screw shank, the bearing between longitudinal support and screw head is not adversely affected by application of the screw head after implantation of the bone screw.

The convex screw head can be formed as one piece with the screw shank or, in the case of a two-piece bone screw, may be connected to the screw shank in a releasable manner. By means of the two-piece design, the means for inserting a screwdriver into the screw shank, for example a hexagon socket or internal thread, can be more easily provided. In addition, in the case of a central arrangement of, for example, a hexagon socket in the screw shank, the bearing between longitudinal support and screw head is not adversely affected by application of the screw head after implantation of the bone screw.

The rim of the collar on the bone screw may be advantageously stepped, especially on the underside toward the screw shank, so that a lower edge is formed which is intended for linear contact with the wall of the concave portion.

Another embodiment of the device differs from the above-described embodiment only in that the collar between screw head and screw shank comprises a plurality of edges concentric to the longitudinal axis of the screw, with diameters $d > d_1 > d_2$ decreasing toward the screw shank.

The edges may be circular on the screw shank side. The diameters $d, d_1, d_2$ preferably may be dimensioned such that the edges run on an imaginary convex surface on the screw shank side and, in the concave portion of the bore, can be made to bear against the wall of the bore at different angles between the longitudinal axis of the screw and the central axis.

The diameters $d, d_1, d_2$ are preferably chosen such that the imaginary surface is a spherical zone concentric to the central axis and with the radius Y.

Depending on the embodiment of the bone screw according to the invention, the diameter D of the concave portion and the diameter d of the collar is advantageously, for example, between 8 mm and 10 mm, or between 4 mm and 6 mm, while the collar advantageously has a thickness, for example, of 1 mm to 2 mm or of 0.5 mm to 1 mm depending on the embodiment of the bone screw according to the invention.

The external diameter of the screw shank advantageously may be, for example, 5 mm to 6 mm or 3 mm to 5 mm depending on the embodiment of the bone screw according to the invention.

In another embodiment of the device according to the invention, the fixation body is designed as a bone plate with at least one through-bore for receiving a bone screw. The device may additionally comprise a grub screw with a means for receiving a screwdriver, the grub screw being able to be screwed in an internal thread introduced from the upper side into the at least one bore and being able to be pressed against the screw head of the bone screw upon tightening. The grub screw alternatively or additionally may comprise means for driving the grub screw into the through-bore of the bone plate.

Advantageously, the invention may provide a bore for receiving a bone screw with a collar which is designed to abut a concave portion of the bore. Further, a linear contact may be obtained which, upon fixation of the device, leads to a secure connection between bone screw and fixation body. In the case of a deformable bore wall, a form-fit connection between collar and bore wall also can be obtained as a result of the linear contact. The advantages which may be afforded by the two-part design of the bone screw include the smooth surface of the convex screw head in the area of contact with another implant part, such as the longitudinal support, and also the contact zone not being impeded by means for receiving a screwdriver.

BRIEF DESCRIPTION OF THE DRAWINGS

Preferred features of the present invention are disclosed in the accompanying drawings, wherein similar reference characters denote similar elements throughout the several views, and wherein:

FIG. 2 shows a partial cross-sectional view of another exemplary embodiment of a device according to the invention, taken parallel to a longitudinal support;

FIG. 3 shows a partial cross-sectional view of the device of FIG. 2 taken transverse to the longitudinal support;

FIG. 4 shows an exemplary embodiment of a multi-part bone fastener according to the invention;

FIG. 5 shows another embodiment of a multi-part bone fastener according to the invention;

FIG. 6 shows yet another embodiment of a multi-part bone fastener according to the invention;

DETAILED DESCRIPTION OF THE PREFERRED EMBODIMENTS

Figure 1:
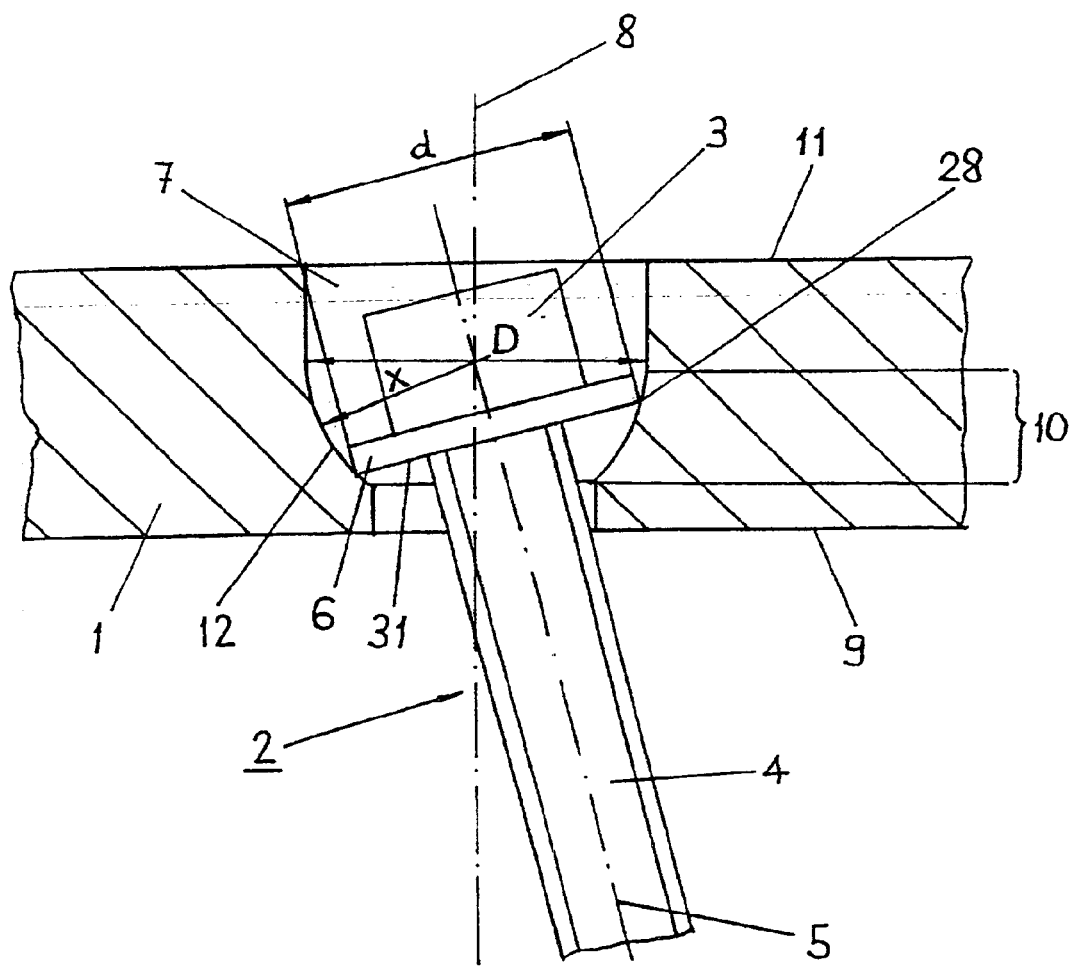
FIG. 1 shows a partial cross-sectional view of an exemplary embodiment of a bone fastener and bone receiving body according to the invention.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

Referring to FIG. 1, a part of a bone fixation body (or receiving member) 1 is shown together with a bone screw 2 according to one exemplary embodiment of the device of the present invention. In this embodiment, the bone fixation body 1 is designed as a bone plate and has an underside 9 toward the screw shank and an upper side 11 toward the screw head. The underside 9 is intended to bear on the bone when the bone plate is screwed tight. The bone screw 2 is received in the bone fixation body 1 in a bore 7, which has a central axis 8. The central axis 8 passes through bone fixation body 1 and is provided with a concave portion 10 tapering toward the underside 9. The concave portion 10 may be of spherical design, with a radius of curvature X, and opens toward the upper side 11 into a cylindrical portion with a diameter D. In this exemplary embodiment, the radius of curvature X corresponds to the radius of the cylindrical portion X=D/2.

Bone screw 2 includes, concentric to a longitudinal axis 5 of the screw, a screw shank 4 to be anchored in the bone or bone part, a screw head 3, and a circular disk-shaped collar 6 arranged between screw shank 4 and screw head 3. The collar 6 is disposed concentric to the longitudinal axis 5 of the screw and has a plane bearing surface 31 toward the screw shank. The outer periphery of plane bearing surface 31 forms a substantially sharp edge 28.

The collar 6 has a diameter d, which is dimensioned such that, in the concave portion 10, it can bear on wall (or inner surface) 12 of bore 7 at different angles between the longitudinal axis 5 of the screw and the central axis 8 of bore 7. This permits bone screw 2 to be screwed into a bone or bone part at different angles relative to bone fixation body 1.

FIG. 2 and FIG. 3 show an exemplary embodiment of the device according to the invention which serves to connect a longitudinal support 13 to a pedicle screw 14 in a spinal column fixation system. This device includes a pedicle screw 14 which has, concentric to its longitudinal axis 24, a screw shank 21 to be anchored in bone and a convex screw head 22. The device also includes a receiving head 15 with a central axis 16. Receiving head 15 serves to connect longitudinal support 13 to pedicle screw 14 and clamping means 25. The clamping means 25, which may have the shape of a nut, is used to fix the longitudinal support 13 and the pedicle screw 14 within the receiving head 15. In this exemplary embodiment, clamping means 25 may be releasably screwed onto receiving head 15 by mating screw threads 31a, 32. In particular, an external thread 31a adjoining upper side 18 of receiving member 15 may mate with an internal thread 32 of clamping means 25.

The convex screw head 22 may be designed in the form of a segment of a sphere, with the zenith 29 of the spherical segment lying on the longitudinal axis 24 of the screw and forming the screw-head end of pedicle screw 14. Also, arranged on screw head 22 may be two or more surfaces 30 oriented parallel to longitudinal axis 24 of the screw and forming two external edges for screwing pedicle screw 14 into bone by means of a screwdriver. An external hexagon is also possible instead of the external two edges.

Receiving head 15 has an upper side 18 toward the screw head, an underside 19 toward the screw shank, a through-bore 17 passing through the receiving head 15 coaxial to the central axis 16 for receiving pedicle screw 14, and additionally a channel 20 extending transverse to central axis 16, open toward upper side 18 and receiving longitudinal support 13. In this way, longitudinal support 13 can be inserted into open channel 20 from the direction of upper side 18 and can be fixed therein in a releasable manner by the clamping member 25.

Through-bore 17 includes a concave portion 26 which tapers toward underside 19 and which, in the exemplary embodiment shown, is designed as a segment of a sphere.

Between convex screw head 22 and the screw shank 21, pedicle screw 14 additionally may be provided with a disk-shaped collar 23 which may be concentric to longitudinal axis 24 of the screw and may be dimensioned such that collar 23, in concave portion 26 of through-bore 17, can bear on wall 27 of through-bore 17 at different angles between longitudinal axis 24 of the screw and central axis 16.

FIG. 4 shows an exemplary embodiment of a two-part bone screw 2 according to the invention. The connection between screw head 3 and screw shank 4 may be a cone connection. Arranged on screw head 3 may be a conical peg 32 which is concentric to longitudinal axis 5 of the screw and which can be secured in a bore 33 concentric to longitudinal axis 5, with an inner cone 34 at the screw head end of screw shank 4.

FIG. 5 shows another exemplary embodiment of a two-part bone screw 2 according to the invention. In this embodiment, the connection between screw head 3 and screw shank 4 is a screw connection. Arranged on the screw head 3 may be a threaded peg 35 which is concentric to longitudinal axis 5 of the screw and which can be screwed into a bore 36, concentric to longitudinal axis 5, with an internal thread 37 at the screw-head end of screw shank 4.

FIG. 6 shows yet another exemplary embodiment of a two-part bone screw 2 according to the invention. The connection between screw head 3 and screw shank 4 in this embodiment is a bayonet lock. Arranged on screw head 3 may be a peg 38, concentric to longitudinal axis 5 of the screw, with a radially protruding pin 39 that may be snapped into a bore 40. A groove 43 may be disposed concentric to longitudinal axis 5, the groove 43 having a part 42 extending parallel to longitudinal axis 5 and a part 41 extending peripherally in bore 40.

Figure 7:
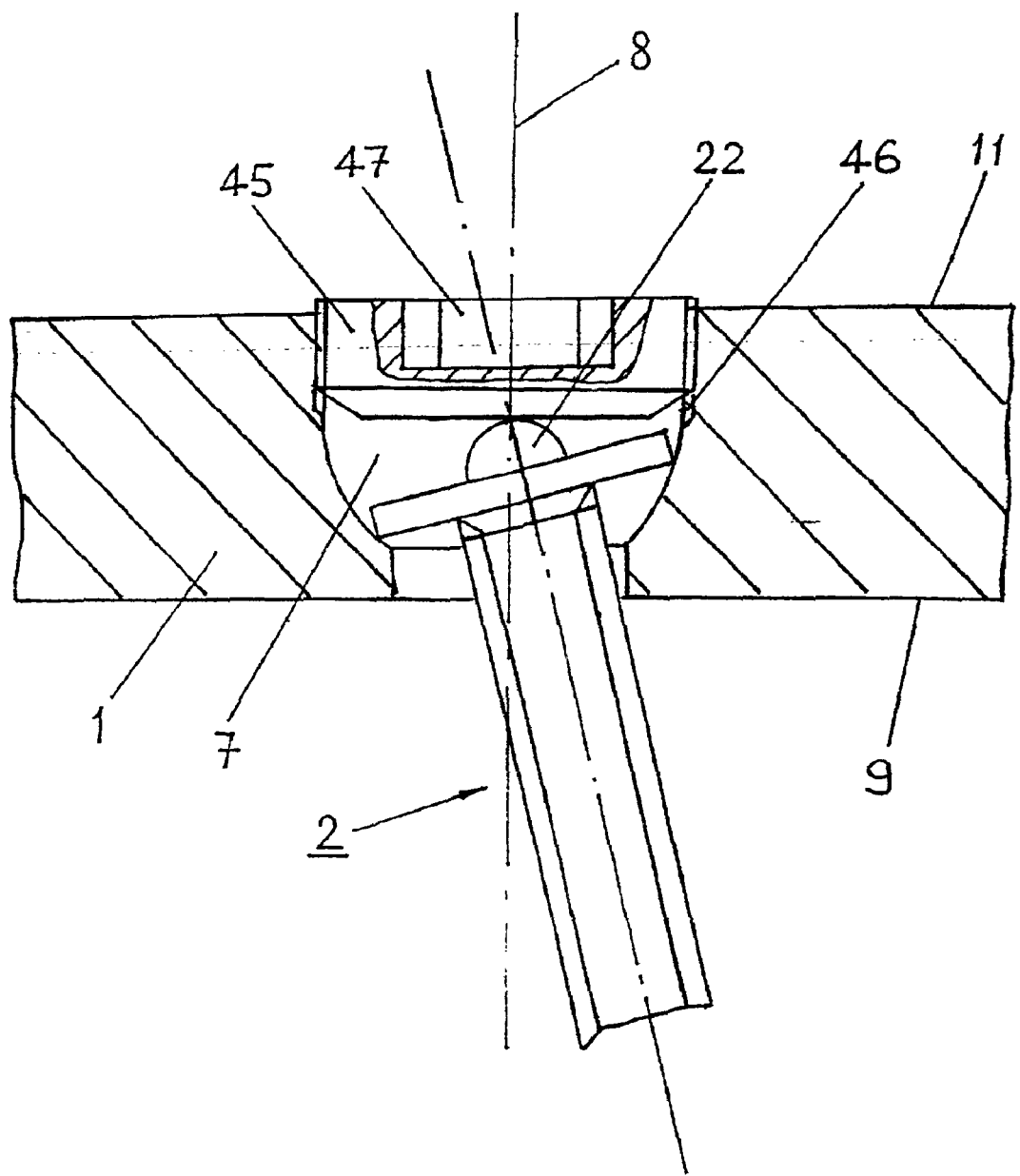
FIG. 7 shows a partial cross-sectional view of another exemplary embodiment of the device according to the invention.

FIG. 7 shows an exemplary embodiment of a device according to the invention which differs from the embodiment shown in FIG. 1 in that fixation body 1 is a bone plate with at least one through-bore 7 for a bone screw 2. In addition, the device includes a grub screw 45 with means 47 for receiving a screwdriver. Grub screw 45 may be screwed in an internal thread 46 and introduced from upper side 11 of bone fixation body 1 into bore 7. Grub screw 45 may be pressed against screw head 22 upon tightening. By means of grub screw 45, which may be tightened, a stable-angle fixation of a bone screw 2 in a bone plate 1 may be achieved.

Figure 8:
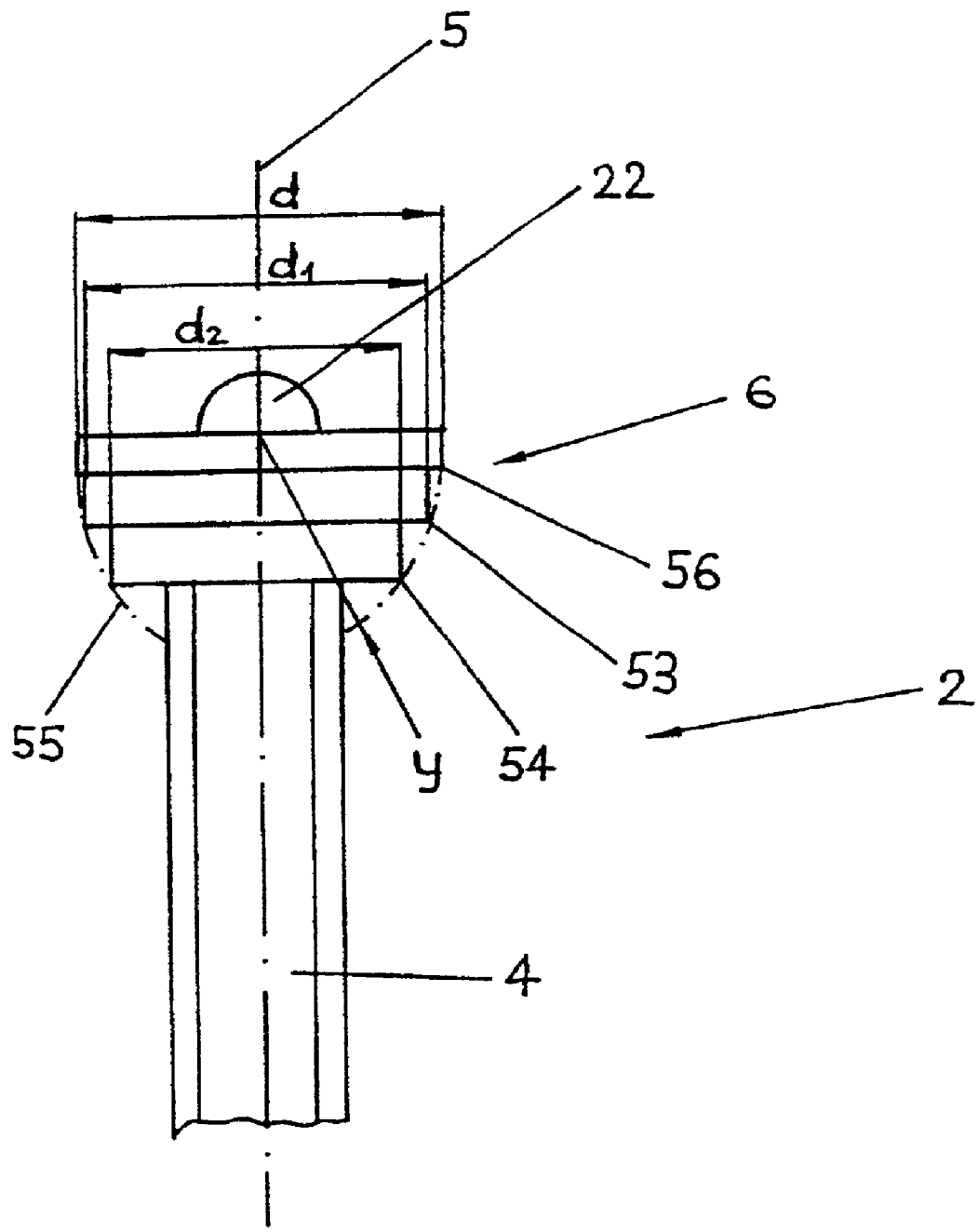
FIG. 8 shows another embodiment of a bone fastener according to the invention.

FIG. 8 shows an exemplary embodiment of a bone screw 2 according to the invention which differs from the embodiments shown in FIGS. 4–6 in that collar 6 is provided with several circular edges 53, 54, 56 toward the screw shank. The diameters d, $d_1$, $d_2$ of these edges 53, 54, 56, respectively, are dimensioned such that edges 53, 54, 56 run on an imaginary convex surface 55, on the screw shank side, which is designed as a spherical zone concentric to central axis 5 and with a radius Y.

FIGS. 1–8 as illustrated and described above, include a bone screw 2; 14 with a screw shank 4; 21 to be anchored concentric to a longitudinal axis 5; 24 of the screw in a bone or bone part, and with a screw head 3; 22. The bone screw 2; 14 has, between the screw head 3; 22 and the screw shank 4; 21, a disk-shaped collar 6; 23 which is concentric to the longitudinal axis 5; 24 of the screw and whose diameter is greater than the diameter of the screw shank 4, 21. The collar 6; 23 may include several edges 53; 54; 56 concentric to the longitudinal axis 5; 24 of the screw. The edges 53; 54; 56 are circular, and the diameters d; $d_1$; $d_2$; $d_i$ are dimensioned such that the edges 53; 54; 56 run on an imaginary convex surface 55 on the screw shank side. The imaginary surface 55 may be a spherical zone concentric to the central axis 8; 16 and with a radius Y.

The rim of a collar 6; 23 may have at least one lower edge 28; 53; 54; 56. Collar 6; 23 may have a plurality of edges 53; 54; 56 concentric to the longitudinal axis 5; 24 of the screw. The concentric edges 53; 54; 56 of the collar 6; 23 may have diameters $d>d_1>d_2$ decreasing toward the screw shank 4. The bone screw 2 may have a screw head 22 of convex design. For example, screw head 22 may be spherical. In particular, screw head 22 may be of semispherical design, the zenith of screw head 22 intersecting longitudinal axis 24 of the screw at the end.

The screw head 3; 22 may be formed as one piece with the screw shank 4; 21. Alternatively, screw 2, 14 may be formed in more than one piece. For instance, at least the screw head 3; 22 and screw shank 4; 21 may be individual parts which may be separate but can be connected concentric to the longitudinal axis 5; 24 of the screw. Screw head 3; 22 and screw shank 4; 21 also may be individual parts which can be connected in a releasable manner. Similarly, screw head 3; 22, collar 6; 23 and screw shank 4; 21 may be individual parts which may be separate but can be connected concentric to longitudinal axis 5; 24 of the screw.

In one embodiment, the screw head 3; 22 may be connected to a screw shank 4; 21 by means of a cone connection. In other embodiments, a screw head 3; 22 may be connected to a screw shank 4; 21 by means of a screw connection or a bayonet lock.

The diameter d of a collar 6; 23 may be, for example, between about 8 mm and about 10 mm, and said collar 6; 23 may have, for example, a thickness of about 1 mm to about 2 mm. The external diameter of a screw shank 4; 21 may be, for example, between about 5 mm to about 6 mm. Preferably, the diameter d of a collar 6; 23 may be, for example, between about 4 mm to about 6 mm, and the thickness of said collar 6; 23 may be between about 0.5 mm to about 1 mm. Typically, the external diameter of a screw shank 4; 21 may be, for example, between about 3 mm to about 5 mm.

In use, the present invention may serve for the fixation of bones or bone parts in an osteosynthesis fixation device. The present invention may also serve for the fixation of bones or bone parts on a bone plate 1. Generally, the device may include a pedicle screw 14 and serve for the fixation of vertebrae in a spinal column fixation device. Such an osteosynthetic bone fixation device may have at least one bone screw 2; 14, as described above, and may further include at least one plate-shaped, prismatic or cylindrical fixation body 1; 15 which has at least one bore 7; 17 with a central axis 8; 16 for receiving said bone screw 2; 14. The fixation body may also have an underside 9; 19 toward the screw shank, and an upper side 11; 18 toward the screw head. The device may further include a bore 7; 17 with a portion 10; 26 tapering toward the underside 9; 19. The diameter d of a collar 6; 23 is dimensioned such that said collar 6; 23, in a concave portion 10; 26 of the bore 7; 17, can be made to bear on a wall 12; 27 of said bore 7; 17 at different angles between a longitudinal axis 5; 24 of the screw and a central axis 8; 16.

Bone screw 2 may be a pedicle screw 14 with a convex screw head 22, and the fixation body 1 may include a receiving head 15 with a central axis 16, which serves to connect a longitudinal support 13 to pedicle screw 14. Receiving head 15 additionally may have a channel 20 extending transverse to the central axis 16 and open toward the upper side 18 in order to receive a longitudinal support 13. The device additionally may have a clamping means 25 which can be connected to the receiving head 15 in a releasable manner from upper side 18 and serve for fixing longitudinal support 13 and pedicle screw 14 within receiving head 15.

Furthermore, a circular collar 6; 23 may have a diameter d, and a concave portion 10; 26 may be of spherical design having a diameter D, where D=d, but alternatively, having a diameter D, where D>d. The ratio d:D may be, for example, between about 0.5 to about 1.0. In some embodiments, the ratio d:D may be between about 0.85 to about 0.95. Additionally, a concave portion 10; 26 may be designed in the manner of a spherical segment, where the spherical segment has a radius X and $X \geq D/2$. The ratio of D/2 to X may be, for example, between about 0.5 to about 1.0, and in some embodiments maybe, for example, between about 0.85 to about 0.95.

In an exemplary embodiment, the rim of a collar 6; 23 is stepped and has at least one lower edge 28; 53; 54; 56. In particular, collar 6 may include a plurality of edges 53; 54; 56 concentric to a longitudinal axis 5; 24 of the screw, with diameters $d>d_1>d_2$ decreasing toward the screw shank 4. Edges 53; 54; 56 may be circular, and diameters d; $d_1$; $d_2$ may be dimensioned such that the edges 53; 54; 56 run on an imaginary convex surface 55 on the screw shank side and, in the concave portion 10; 26 of a bore 7; 17, can be made to bear on a wall 12; 27 of said bore 7; 17 at different angles between a longitudinal axis 5; 24 of the screw and a central axis 8; 16. More particularly, imaginary surface 55 may be a spherical zone concentric to a central axis 8; 16 and with a radius Y.

Fixation body 1 may be a bone plate having at least one through-bore 7 for a bone screw 2, and additionally may include a grub screw 45 with means for driving the grub screw into bore 7 of the bone plate. Grub screw 45 may be screwed in an internal thread 46 and introduced from the upper side 11 into the bore 7, and maybe pressed against a screw head 22 upon tightening.

While various descriptions of the present invention are described above, it should be understood that the various features can be used singly or in any combination thereof. Therefore, this invention is not to be limited to only the specifically preferred embodiments depicted herein. For instance, other suitable positive engagement systems may be employed. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A bone fixation assembly comprising:
   a bone fastener comprising a head, a shank sized and configured to be anchored into bone, and at least one collar arranged in-between the head and shank, the at least one collar having a top surface, a bottom surface and a lateral sidewall extending between the top surface and the bottom surface, the intersection of the lateral sidewall with the bottom surface forming a substantially sharp edge; and
   a receiving member comprising at least one bore that defines an inner surface having a first portion and a second portion, the first portion has a substantially constant diameter and the second portion is substantially concave;
   wherein the sharp edge of the at least one collar contacts the concave second portion of the receiving member so that the bone fastener can he variably positioned with respect to the receiving member.

2. The bone fixation assembly of claim 1, wherein the concave portion has a radius of curvature and the ratio of half the diameter of the first portion to the radius of curvature is between about 0.5 and about 1.0.

3. The bone fixation assembly of claim 2, wherein the ratio of half the diameter of the first portion to the radius of curvature is between about 0.85 and about 0.95.

4. The bone fixation assembly of claim 1, wherein the fastener has a longitudinal axis and the at least one collar has a generally circular cross-section transverse to the longitudinal axis.

5. The bone fixation assembly of claim 4, wherein the at least one collar has a substantially constant diameter.

6. The bone fixation assembly of claim 5, wherein the at least one collar has a diameter between about 4 mm and about 10 mm.

7. The bone fixation assembly of claim 5, wherein the at least one collar has a combined thickness between about 0.5 mm and about 2 mm.

8. The bone fixation assembly of claim 1, wherein the fastener head is convex with respect to the shank.

9. The bone fixation assembly of claim 8, wherein at least a portion of the fastener head is substantially semispherical.

10. The bone fixation assembly of claim 1, wherein the fastener head is integrally formed with the shank.

11. The bone fixation assembly of claim 1, wherein the fastener head is removably attached to the shank.

12. The bone fixation assembly of claim 1, further comprising a clamping member, wherein the clamping member is capable of locking the bone fastener with respect to the receiving member in a fixed configuration.

13. The bone fixation assembly of claim 12, wherein the clamping member is a grub screw.

14. The bone fixation assembly of claim 12, wherein the clamping member is releasably associated with the receiving member for releasably locking the assembly in a fixed configuration.

15. The bone fixation assembly of claim 12, wherein the clamping member is threadably associated with the receiving member.

16. The bone fixation assembly of claim 1, wherein the inner surface comprises a deformable material such that a form-fit connection is obtainable between the at least one collar and the receiving member.

17. The bone fixation assembly of claim 1, wherein the receiving member further comprises a channel extending transverse to a central axis of the bore, the channel configured and dimensioned to receive a longitudinal support.

18. The bone fixation assembly of claim 1, wherein the first portion is cylindrical and the concave portion is spherical.

19. The bone fixation assembly of claim 1, wherein the receiving member is a bone plate.

20. The bone fixation assembly of claim 19, wherein the bore formed in the bone plate includes an internally threaded portion for receiving a grub screw so that rotation of the grub screw presses the grub screw against the head of the bone fastener to fix the position of the bone fastener with respect to the bone plate.

21. The bone fixation assembly of claim 1, wherein the receiving member interconnects the bone fastener to a longitudinal spinal rod.

22. The bone fixation assembly of claim 21, wherein the receiving member further includes a transverse channel for receiving the longitudinal spinal rod and clamping means for fixing the position of the longitudinal spinal rod with respect to the bone fastener.

23. The bone fixation assembly of claim 1, wherein the head of the fastener is removably attached to the shank of the fastener.

24. The bone fixation assembly of claim 23, wherein the head of the fastener includes a conical peg and the shank of the fastener includes a bore so that the head is attached to the shank by a cone connection.

25. The bone fixation assembly of claim 23, wherein the head of the fastener includes a threaded peg and the shank of the fastener includes a threaded bore so that the head is attached to the shank by a screw connection.

26. The bone fixation assembly of claim 23, wherein the head of the fastener includes a peg with a radially protruding pin and the shank of the fastener includes a bore with a groove sized and configured to receive the pin so that the head is attached to the shank by a bayonet type connection.

27. The bone fixation assembly of claim 1, wherein the fastener includes a plurality of collars, each collar being arranged in-between the head of the bone fastener and the shank of the bone fastener.

28. The bone fixation assembly of claim 27, wherein each collar is circular with a diameter and the shank of the fastener has a diameter, the diameters of the collar being greater than the diameter of the shank.

29. The bone fixation assembly of claim 28, wherein the collars are arranged so that the diameter of the collars decrease as one moves from the head of the fastener towards the shank of the fastener so that the collars form a plurality of stepped edges.

30. The bone fixation assembly of claim 29, wherein the stepped edges of the collars form an imaginary convex surface.

31. The bone fixation assembly of claim 28, wherein the concave portion of the bore has a diameter D so that the diameter of the collars are less than diameter D of the bore.

32. The bone fixation assembly of claim 31, wherein the ratio of the diameters of the collars to the diameter D of the bore 0.5 to 1.0.

33. The bone fixation assembly of claim 32, wherein the ratio of the diameters of the collars to the diameter D of the bore is 0.85 to 0.95.

34. A device for osteosynthetic bone fixation comprising:
a bone fastener comprising a plurality of collars and a shank sized and configured to be anchored into bone, each collar having a top planar surface, a bottom planar surface and a lateral sidewall extending between the top surface and the bottom surface, the intersection of the lateral sidewall with the bottom surface forming a substantially sharp edge; and
a receiving member comprising at least one bore that defines an inner surface with a first cylindrical portion and a second non-cylindrical portion,
wherein the sharp edges of the collar abuts the non-cylindrical portion at a selectable angle.

35. The device of claim 34, wherein the bone fastener has a longitudinal axis and the collar are disposed generally concentric to the longitudinal axis.

36. The device of claim 35, wherein the sharp edges are disposed generally concentric to the longitudinal axis.

37. The device of claim 36, wherein the sharp edges form a substantially circular line and wherein each edge is disposed along an imaginary convex surface.

38. The device of claim 37, wherein the imaginary convex surface is spherical.

39. The device of claim 35, wherein each collar has a substantially constant diameter.

40. The device of claim 39, wherein the diameters are is between about 4 mm and about 10 mm.

41. The device of claim 35, wherein the collars have a combined thickness between about 0.5 mm and about 2 mm.

42. The device of claim 35, wherein the bone fastener further comprises a head that is convex with respect to the shank.

43. The device of claim 42, wherein at least a portion of the head is substantially semispherical.

44. The device of claim 42, wherein the head is integrally formed with the shank.

45. The device of claim 42, wherein the fastener head is removably attached to the shank.

46. The device of claim 35, wherein the receiving member further comprises a channel extending transverse to a central axis of the bore, the channel configured and dimensioned to receive a longitudinal support.

47. The device of claim 34, further comprising a clamping member, wherein the collar is releasably lockable by the clamping member.

48. The device of claim 47, wherein the clamping member is a grub screw.

49. The device of claim 47, wherein the clamping member is a nut.

50. A bone fixation system comprising:
a bone screw having a longitudinal axis,
a head;
a shank; and
a collar disposed between the head and shank and comprising a top portion and a plurality of lower portions, at least two adjacent lower portions forming at least one edge generally concentric to a longitudinal axis of the bone screw, wherein each edge is disposed along an imaginary convex surface that is generally spherical; and
a receiving member comprising at least one bore having a longitudinal axis, the bore defining an inner surface having an upper portion and a lower generally spherical portion for contacting the imaginary convex surface for permitting the longitudinal axis of the bone screw to be angulated with respect to the longitudinal axis of the bore.

51. The bone screw of claim 50, wherein the collar has two edges.

52. The bone screw of claim 51, wherein at least a portion of the head is substantially semispherical.

53. The bone screw of claim 52, wherein the head is integrally formed with the shank.

54. The bone screw of claim 52, wherein the head and shank are separately formed.

55. The bone screw of claim 54, wherein the head is releasably associated with the shank.

56. The bone screw of claim 54, wherein the head is threadably associated with the shank.

57. The bone screw of claim 54, wherein the head is connected to the shank by a conical peg that is received in a conical bore, with the conical peg and conical bore being disposed along the longitudinal axis.

58. The bone screw of claim 54, wherein the head is connected to the shank by a bayonet lock.

59. The bone screw of claim 52, wherein the bead further comprises a zenith disposed on the longitudinal axis.

60. The bone screw of claim 50, wherein each edge has a diameter, and the diameters of the edges decrease as a function of increasing distance from the head.

61. The bone screw of claim 60, wherein the collar is disk-shaped.

62. The bone screw of claim 50, wherein the head is convex with respect to the shank.

63. The bone screw of claim 50, wherein each edge forms a generally circular shape having a diameter between about 4 mm and about 10 mm.

64. The bone screw of claim 50, wherein each edge forms a generally circular shape having a diameter between about 8 mm and about 10 mm.

65. The bone screw of claim 50, wherein the collar has a thickness defined between a top surface and a bottom surface between about 0.5 mm and about 2 mm.

66. The bone screw of claim 50, wherein the shank has an external diameter between about 3 mm and about 6 mm.

67. The bone screw of claim 50, wherein each edge forms a substantially circular shape.

68. The bone screw of claim 50, wherein each edge is substantially sharp.

69. A bone fixation assembly comprising;
a bone fastener comprising a head, a shank having threads to be anchored into bone, and a plurality of disk-shape collars, each collar having a top surface, a bottom surface and a lateral sidewall extending between the top surface and the bottom surface, the intersection of the lateral sidewall with the bottom surface forming a substantially sharp edge; and
a receiving member comprising at least one bore that defines an inner surface with a first cylindrical portion and a second non-cylindrical portion,
wherein the diameters of the collars are sized and configured so that they decrease from the head to the shank so that the sharp edges of the collars form an imaginary convex surface, each of the sharp edges containing the second non-cylindrical portion.

* * * * *

UNITED STATES PATENT AND TRADEMARK OFFICE
CERTIFICATE OF CORRECTION

PATENT NO. : 6,893,443 B2  
DATED : May 17, 2005  
INVENTOR(S) : Frigg et al.

It is certified that error appears in the above-identified patent and that said Letters Patent is hereby corrected as shown below:

Column 11,  
Line 35, please replace "he" with -- the --;

Column 12,  
Line 61, please replace "diameter" with -- diameters --;

Column 13,  
Line 3, please insert -- the -- before "diameter D";  
Line 21, please replace "collar abuts" with -- collars abut --;  
Line 24, please replace "collar" with -- collars --;  
Line 34, please delete "is";

Column 14,  
Line 26, please replace "bead" with -- head --;  
Line 52, please replace "disk-shape" with -- disk-shaped --;  
Line 64, please replace "containing" with -- contacting --.

Signed and Sealed this

Twenty-fifth Day of October, 2005

JON W. DUDAS  
*Director of the United States Patent and Trademark Office*